US006335323B2

(12) United States Patent
Worsley

(10) Patent No.: US 6,335,323 B2
(45) Date of Patent: *Jan. 1, 2002

(54) COMPOSITIONS FOR THE TREATMENT OF PERIPHERAL NEUROPATHIES CONTAINING ANTIDEPRESSANTS AND/OR MONOAMINE OXIDASE INHIBITORS AND/ OR VITAMIN B12 AND/OR PRECURSORS OR INDUCERS OF A NEUROTRANSMITTER

(75) Inventor: Andrew Peter Worsley, Farnborough (GB)

(73) Assignee: The WWK Trust, Kent (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,314
(22) PCT Filed: Jul. 4, 1997
(86) PCT No.: PCT/GB97/01822
  § 371 Date: Mar. 4, 1999
  § 102(e) Date: Mar. 4, 1999
(87) PCT Pub. No.: WO98/01157
  PCT Pub. Date: Jan. 15, 1998

(30) Foreign Application Priority Data

Jul. 5, 1996 (GB) .............................. 9614121
Jul. 31, 1996 (GB) .............................. 9616019

(51) Int. Cl.$^7$ .......................... A61K 31/70; A61K 31/55
(52) U.S. Cl. ........................... 514/52; 514/43; 514/210; 514/213; 514/217; 514/646
(58) Field of Search ........................... 514/43, 52, 360, 514/217, 213, 210, 646

(56) References Cited

U.S. PATENT DOCUMENTS 3,981,863 A * 9/1976 Niswender et al. ........... 536/25
4,431,670 A    2/1984 Heller
4,652,559 A    3/1987 Szmuszkovicz

FOREIGN PATENT DOCUMENTS

WO    96/11009    * 4/1996    ......... A61K/31/645

* cited by examiner

*Primary Examiner*—Gary Geist
*Assistant Examiner*—Howard V. Owens, Jr.
(74) *Attorney, Agent, or Firm*—Larson & Taylor PLC

(57) ABSTRACT

Methods and compositions for treatment of a patient suffering from a form of peripheral neuropathy are disclosed. The method comprises administering to the patient any one of the following combinations of components: I. A, B and C; II. A and B; III. B and C; IV. A and C, wherein A is an antidepressant or a monoamine oxidase inhibitor, B is vitamin $B_{12}$, and C is a precursor or inducer of a neurotransmitter, e.g. L-phenylalanine.

11 Claims, No Drawings

COMPOSITIONS FOR THE TREATMENT OF PERIPHERAL NEUROPATHIES CONTAINING ANTIDEPRESSANTS AND/OR MONOAMINE OXIDASE INHIBITORS AND/ OR VITAMIN B12 AND/OR PRECURSORS OR INDUCERS OF A NEUROTRANSMITTER

TECHNICAL FIELD

The present invention relates to the use of a combined medicament in the treatment of various forms of peripheral neuropathy, especially painful neuropathies and diabetic neuropathy, including diabetic amyotrophy, mononeuritis, mononeuritis multiplex, cranial nerve palsies and autonomic neuropathy. The invention also relates to the preparation of medicaments for such treatments.

BACKGROUND OF THE INVENTION AND PRIOR ART

Diabetes mellitus is a metabolic disorder resulting in hyperglycaemia (raised blood sugar), polyuria (increased output of urine) and glycosuria (appearance of sugars (e.g. glucose) in the urine). Diabetes has been recognised as a major disease for centuries. In addition to defective carbohydrate metabolism, it can also lead to altered metabolism of lipids and proteins and patients are at risk of complications from microvascular and macrovascular diseases which are serious and may be fatal.

Insulin dependent diabetes results from failure of the islets of Langerhans ($\beta$) cells of the pancreas to produce sufficient insulin. This often arises as a result of autoimmunity directed against islet tissue. Non-insulin-dependent diabetes may in part arise from altered efficiency of insulin receptor signalling (insulin resistance) or from a relative deficiency of insulin.

Detectable diabetic neuropathy occurs in approximately 60% of diabetic patients. Some 20% of diabetic patients show moderate to severe symptoms, the severity is generally thought to be linked to the duration of diabetic symptoms and the level of control using e.g. insulin, or oral hypoglycaemic agents such as the sulphonylureas.

Diabetic neuropathy may be mild, for example taking the form of "burning" or tingling in the feet or numbness and/or loss of vibration sense in the extremities, especially the feet. Moderate to severe symptoms of neuropathy include pain and spasm in the extremities (painful neuropathy with spasm). Diabetic amyotrophy is indicated by pain over the thigh and loss of quadriceps power, sometimes also loss of power in the lower leg resulting in foot drop. Autonomic neuropathy principally affects the nerves supplying the heart and viscera. Mononeuritis is usually caused by a single peripheral nerve palsy.

Other peripheral neuropathies include the following:

HIV associated neuropathy;
$B_{12}$-deficiency associated neuropathy;
cranial nerve palsies;
drug-induced neuropathy;
industrial neuropathy;
lymphomatous neuropathy;
myelomatous neuropathy;
multi-focal motor neuropathy;
chronic idiopathic sensory neuropathy;
carcinomatous neuropathy;
acute pan autonomic neuropathy;
alcoholic neuropathy;
compressive neuropathy;
vasculitic/ischaemic neuropathy;
mono- and poly- neuropathies.

Both type I (insulin dependent) diabetes and type II (non-insulin dependent) diabetes are associated with neuropathy. Type I diabetes commonly presents in relatively young adults, often with diabetic ketoacidosis, type II diabetes (also know as maturity onset diabetes) often occurs in middle age or in elderly patients. Type II diabetes is particularly associated with the relatively late and severe onset of neuropathy.

Previous treatments for diabetic neuropathy have included tricyclic antidepressants on their own, the antiepileptic drug carbemazepine, and the antiarrythmic drug mexilitene. However these seem only to be mildly effective, and not in all cases. Long term good diabetic control has also shown to be a benefit in the prevention of diabetic neuropathy and in control of the symptoms, presumably controlling the agents which cause the damage to the nerves. There is little indication that long term control of diabetes can reverse symptoms i.e. the damage, once done, appears not to be reversible by treatment of the underlying diabetes.

Recent clinical trials have shown that gamolenic acid may reduce symptoms, and prevent the progression of abnormalities in nerve conduction studies in diabetic neuropathy.

WO 96/11009 discloses treatment of multiple sclerosis by some of the combinations of components employed in the present invention.

Vitamin $B_{12}$ has been proposed for the treatment of $B_{12}$-deficiency associated neuropathy.

DISCLOSURE OF THE INVENTION

The present inventor has surprisingly found that a combination of an antidepressant or a monamine oxidase inhibitor (MAOI) with an inducer or a precursor of a neurotransmitter can be effective in the treatment of peripheral neuropathies, and in particular painful neuropathy. The components of this medicament may be presented as a combined preparation for simultaneous, separate or sequential use in the treatment of various peripheral neuropathies. It has also been observed that a parallel or simultaneous administration of vitamin $B_{12}$ treatment, for example orally or by injection, may enhance the therapeutic effect of this combination.

It has also been found that combinations (i) vitamin $B_{12}$ with an inducer or a precursor of a neurotransmitter and (ii) vitamin $B_{12}$ with an antidepressant, are effective in treatment of peripheral neuropathies.

Accordingly, in a first aspect the present invention provides the use of any one of the following components or combinations of components:

C,
A and B,
A and C,
B and C,
A, B and C,
wherein
A is an antidepressant or a monoamine oxidase inhibitor,
B is vitamin $B_{12}$, and
C is a precursor or inducer of a neurotransmitter, in the manufacture of a medicament for the treatment of at least one form of peripheral neuropathy.

In another aspect the invention provides a method of making a medicament for the treatment of a patient suffering from a peripheral neuropathy, comprising admixing any one of the following components:

C,

A and B,

A and C,

B and C,

A, B and C, wherein

A is an antidepressant or a monoamine oxidase inhibitor,

B is vitamin $B_{12}$, and

C is a precursor or inducer of a neurotransmitter, with at least one pharmaceutically acceptable component or vehicle to prepare a medicament suitable for administration to a patient.

In yet another aspect the invention provides a method of treatment of a patient suffering from a form of peripheral neuropathy, comprising administering to the patient any one of the following combinations of components:

I. A, B and C

II. A and B

III. B and C

IV. A and C wherein

A is an antidepressant or a monoamine oxidase inhibitor,

B is vitamin $B_{12}$, and

C is a precursor or inducer of a neurotransmitter, said components being administered simultaneously or separately, in amounts which in combination have the effect of ameliorating the peripheral neuropathy.

In a further aspect the invention provides a pharmaceutical composition containing as the only pharmaceutically active components vitamin $B_{12}$ and a precursor or inducer of a neurotransmitter.

Treatment may be simultaneous or separate including sequential administration of the components.

In the medicaments of the invention, there may be included at least one pharmaceutically acceptable component or vehicle such as an incipient, carrier, buffer, stabiliser or other material, as discussed below.

Also provided is a kit or pack containing components A and B, or A and C, or A and B and C, or B and C, wherein component A the components being formulated for simultaneous, separate or sequential delivery in the treatment of peripheral neuropathy. Particularly components A and C may be combined, and component B separate.

The diabetic neuropathy with which the present invention is concerned may be characterised by degeneration of the long nerves (the nerves of the peripheral nervous system) as a result of the metabolic disturbances of diabetes. This can be contrasted with other neurodegenerative disorders such as multiple sclerosis, the effects of which are concentrated in the central nervous system. Whilst multiple sclerosis leads to demyelination of the neurons of the central nervous system (that is, degeneration of the myelin sheath which surrounds the neurons), the toxic effects of diabetes occur in the body of the peripheral neuron, possibly due to the toxic effect of metabolites arising through the underlying diabetic disturbance of carbohydrate metabolism, or as a secondary effect of diabetic microvascular degeneration. Whatever the mechanism, the result of the degenerative changes in the body of the peripheral neuron is reduced signal conductivity along the length of the nerve. It is believed that the initial generation of a signal and the passage of a signal across synapses may not be directly effected by the condition.

In addition to diabetic neuropathies, the present invention is applicable to any and all of peripheral neuropathies, particularly painful neuropathies, including those listed above in the introduction.

Preferred antidepressants for use in the present invention include tricyclic and tetracyclic antidepressants such as lofepramine and selected seritonin re-uptake inhibitors (SSRI). Lofepramine and certain other tricyclic antidepressants also show some monoamine oxidase inhibitor (MAOI) activity. Other suitable antidepressants and MAOIs include mianserin, trimipramine, imipramine, clomipramine, amitriptyline, protriptyline, nortriptyline, fluvoxamine, fluoxetine, maprotiline, sertaline, venlaflaxine, pargyline, triazolopyridine, phenelzine, tranylcypromine, desipramine, moclopemide, dothiepin, doxepin, paroxetine, oxazine or viloxazine, amongst others.

A neurotransmitter inducer is a component which enhances or triggers production of a neurotransmitter.

A preferred neurotransmitter precursor for use in the present invention is L-phenylalanine (LPA). However L-tryptophan may also find use in the present invention.

Other amino acids such as L-tyrosine or other compounds such as tyramine may also find use in the present invention as a neurotransmitter, inducer or precursor.

Compounds may be provided as a metabolite of a precursor. For example, L-phenylalanine may be provided as a metabolite of aspartame.

If the combination for treatment includes vitamin $BL_2$, this may be in the form of cyanocobalamin or hydroxycobalamin, to be administered orally or intramuscularly.

The compositions provided herein may comprise an antidepressant or a monoamine oxidase inhibitor (MAOI) and a neurotransmitter precursor or inducer, or any other combination of components disclosed herein, as combined (simultaneous or sequential) actives. However, compounds may be employed which mimic a given active in improving diagnostic status and/or ameliorating one or more symptoms of diabetic neuropathy (mimetics). Such compounds and their use are within the scope of the present invention. Also within the scope of the present invention are derivatives or analogues of the antidepressant or MAOI which retain the antidepressant or MAOI activity, respectively.

In accordance with the present invention, compositions provided may be administered to individuals. Administration is preferably in a "therapeutically effective amount", this being sufficient to show benefit to a patient. Such benefit may be at least amelioration of at least one symptom. The actual amount administered, and rate and time-course of administration, will depend on the nature and severity of what is being treated. Prescription of treatment, eg decisions on dosage etc, is within the responsibility of general practitioners and other medical doctors. Dose regimens for the MAOIs and antidepressants may be within the range used for the treatment of depression (for which the standard starting dose of lofepramine is 140 mg per day). With the proviso that the prescribing physician will be able to decide suitable and safe dosage levels, a possible range for administration of antidepressants is 10–210 mg per day, although 50–70 mg per day may be suitable. For the neurotransmitter precursors or inducers, a range of 100 mg to 5 g per day, preferably 500–2000 mg/d (mg per day) may be employed, the dose increasing in proportion to the level of antidepressant or MAOI employed.

As an example, a 70 mg dose of lofepramine may be combined with 500 mg of L-phenylalanine given in the morning, this being supplemented with a further 500 mg of L-phenylalanine given in the afternoon.

Where vitamin $B_{12}$ is co-administered, the amounts may be those generally recommended for daily intake of the vitamin or may be greater than that recommended as average daily intake. The preferred average dosage range for vitamin $B_{12}$ in the invention is from 1 mg every 3 months up to 1 mg every 3 days. When symptoms are severe, this may be 1 mg intramuscular hydroxycobalamin per week in an 8–10 week course at the start of treatment, perhaps reduced to 1 mg every 10 days as treatment progresses. The desired dosage level of vitamin $B_{12}$ may conveniently be given by weekly intramuscular injection, but doses ranging from 5 μg to 10 mg may be given daily orally.

Pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous or intravenous.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required. L-tryptophan and L-phenylalanine are available in 500 mg tablets.

A combined oral preparation in single tablet form, containing all these components A, B and C, or for example components B and C, is feasible. Alternatively, a treatment pack may contain the components separately.

EXAMPLES

Case #1

A 48 year old male, diagnosed non-insulin dependent diabetic when aged 28, showed symptoms of diabetic neuropathy which commenced approximately 8 years ago. The onset of neuropathy was thought to be due to poor control of diabetes. Neuropathic symptoms increased in severity over several years with development of severe diabetic neuropathy including diabetic amyotrophy, painful neuropathy with spasm, diabetic autonomic neuropathy and decreased sensation in the extremities, with numbing and loss of vibration sense. Electromyography confirmed the diagnosis of diabetic neuropathy.

Treatment with tricyclic antidepressants and carbemazepine was ineffective. An improvement in control of the patient's diabetes also did not significantly affect his severe symptoms.

A regime of 70 mg lofepramine and 500 mg LPA, each administered with informed consent twice daily, with weekly 1 mg vitamin $B_{12}$ injections, significantly improved reported symptoms within 12 hours. Almost complete clinical resolution of clinical signs and symptoms had occurred after one week of combined therapy.

Long term maintenance of diabetic neuropathic remission has required continued treatment, for this patient.

Case #2

A 55 year old male with non-insulin dependent diabetes with very severe diabetic neuropathy, including diabetic amyotrophy and bedbound, resistant to current therapies, was commenced on vitamin $B_{12}$ injections (1 mg at two-week intervals) and L-phenylalanine (as a metabolite of aspartame) 500 mg twice a day.

Benefit in amyotrophy was noted within 3 hours of commencement of treatment. The subsequent addition of lofepramine 70 mg twice daily produced a further improvement. Within 3 weeks his diabetic amyotrophy was considerably improved.

Case #3

This case studied here is of the same 48 year old male with diabetic neuropathy as in case #1, but after the original observation in case #1. The patient was subsequently continued on the same vitamin $B_{12}$ injections and phenylalanine (500 mg twice daily) only. He continued to benefit from his therapy whilst on these two drugs only, for approximately two months, and then required the recommencement of lofepramine to maintain good effect clinically.

Case #4

A 72 year old male with vitamin $B_{12}$ neuropathy and mild alcoholic neuropathy was studied.

Clinical progress with vitamin $B_{12}$ injections alone was insignificant. The addition of lofepramine to the medication enabled the patient to retain his balance, lose his painful neuropathy, and within 3 days ambulate almost normally. Previously he required the assistance of another person to walk.

Case #5

A 76 year old female with non-insulin dependent diabetes for 15 years with reasonable control, developed peripheral painful diabetic neuropathy of two months duration. She was commenced with vitamin $B_2$ 1 mg weekly, L-phenylalanine 500 mg twice daily and lofepramine 35 mg twice daily (reduced dosage because of age) with a very good response within 48–72 hours. All symptoms had disappeared. The treatment was stopped six weeks after the commencement of the therapy and there has been no recurrence in the two months to the time of report of this case.

Case #6

A 50 year old male who had diabetes for 15 years more recently requiring insulin therapy, developed peripheral painful diabetic neuropathy which had become severe, he was commenced on vitamin $B_{12}$ 1 mg intramuscular weekly, lofepramine 70 mg twice daily and L-phenylalanine 500 mg twice daily. He had a good response within the first two weeks. After that period treatment was stopped and he had no recurrence of symptoms and there were no side effects detected.

Case #7

A 59 year old male with peripheral diabetic neuropathy and impotence of 3 years duration becoming increasingly severe over three months period prior to therapy. He was commenced on weekly vitamin $B_{12}$ 1 mg intramuscular, lofepramine 70 mg twice daily and L-phenylalanine 500 mg twice daily. He had a good immediate response within the first two weeks with no side effects. He continues with his treatment at the time of report of this case.

Case #8

A male in his fourth decade had mild painful peripheral alcoholic neuropathy of six months duration with increasing severity over the past two months. In addition he complained of a compressive neuropathy involving the C6 nerve root. He was commenced on vitamin $B_{12}$ orally 200 μg daily and L-phenylalanine 500 mg twice daily with a considerable reduction in symptomatology whilst on therapy.

Case #9

A male in his fifth decade was HIV positive and complained of moderate peripheral neuropathy including painful neuropathy. He also had mild diabetes of short duration but clinically his neuropathy was diagnosed as that related to HIV. He had been previously commenced on amitriptyline 75 mg daily with some mild beneficial effects. He was additionally commenced on L-phenylalanine 500 mg twice daily, whereafter he reported an approximate further 50% improvement in the symptoms of his painful neuropathy.

Case #10

A female in her sixth decade had severe diabetic peripheral neuropathy and resultant Charcot foot joints. She was initially placed on tricyclic anti-depressants in the form of dothiepin 150 mg once daily with a mild beneficial effect. The subsequent addition of vitamin $B_{12}$ injections 1 mg weekly, resulted in improvement in painful symptomatology. Vibration sense was also improved. Further clinical benefit was gained by the addition of L-phenylalanine 500 mg twice daily. Vibration sense initially could not be detected at a level below the knee. During therapy the level at which vibration sense which could be detected was at the level of the medial malleolus. Her pain has subsided and she has noted no further progression in the damage to her joints to date of reporting of this case.

It will be apparent to those skilled in the art that variations and modifications to the specific embodiments disclosed herein may be made without departing from the scope of the invention.

What is claimed is:

1. Method of treatment of a patient suffering from a form of peripheral neuropathy, wherein the peripheral neuropathy is selected from the group consisting of:
    diabetic neuropathy,
    mononeuritis,
    mononeuritis multiplex,
    alcoholic neuropathy,
    HIV associated neuropathy,
    $B_{12}$-deficiency associated neuropathy,
    lymphomatous neuropathy,
    chronic idiopathic sensory neuropathy,
    carcinomatous neuropathy,
    acute pain autonomic neuropathy,
    compressive neuropathy and
    vasculitic/ischaemic neuropathy,
    comprising administering to the patient any one of the following combinations of components:
        I. A, B and C
        II. A and B
        III. B and C
        IV. A and C
            wherein
            A is an antidepressant or a monoamine oxidase inhibitors,
            B is vitamin $B_{12}$, and
            C is a precursor or inducer of a neurotransmitter, selected from the group consisting of L-phenylalanine, L-tyrosine, L-tryptophan and tyramine,
    said components being administered simultaneously or separately, in amounts which in combination have the effect of ameliorating the peripheral neuropathy.

2. Method according to claim 1 wherein the neuropathy is a painful neuropathy.

3. Method according to claim 1 wherein the neuropathy is diabetic neuropathy.

4. Method according to claim 1. wherein A is a tricyclic or tetracyclic antidepressant or a selected seritonin re-uptake inhibitor.

5. Method according to claim 4, wherein A is lofepramine.

6. Method according to claim 1, wherein B is in the form of cyanocobalamin or hydroxycobalamin.

7. A pharmaceutical composition containing as the only pharmaceutically active components vitamin $B_{12}$ and a precursor or inducer of a neurotransmitter selected from the group consisting of L-phenylalanine, L-tyrosine, L-tryptophan and tyramine.

8. A pharmaceutical composition according to claim 7 wherein vitamin $B_{12}$ is in the form of cyanocobalamin or hydroxycobalamin.

9. A method according to claim 3 herein the diabetic neuropathy is one of diabetic amytrophy and diabetic autonomic neuropathy.

10. A pharmaceutical composition as in powder, tablet, capsule or liquid form, wherein the composition contains at least 100 mg of a precursor or inducer of a neurotransmitter selected from the group consisting of L-phenylalanine, L-tyrosine, L-tryptophan and tyramine, and at least 5 μg of vitamin $B_{12}$ as the only pharmaceutically active components.

11. A pharmaceutical composition containing as the only pharmaceutically active components vitamin $B_{12}$ and a precursor or inducer of a neurotransmitter selected from the group consisting of L-phenylalanine, L-tyrosine, L-tryptophan and tyramine, which further comprises a pharmaceutically acceptable excipient, carrier, buffer or stabilizer.

* * * * *